(12) United States Patent
Tirio et al.

(10) Patent No.: US 9,028,590 B2
(45) Date of Patent: May 12, 2015

(54) PROCESS AND APPARATUS FOR CARBON DIOXIDE AND CARBONYL SULFIDE CAPTURE VIA ION EXCHANGE RESINS

(71) Applicants: LANXESS Sybron Chemicals Inc., Birmingham, NJ (US); LANXESS Deutschland GmbH, Leverkusen (DE)

(72) Inventors: Anthony P. Tirio, Pittsburgh, PA (US); Rudolf Wagner, Cologne (DE)

(73) Assignees: LANXESS Deutschland GmbH, Cologne, DE (US); LANXESS Sybron Chemicals, Inc., Birmingham, NJ (US)

( * ) Notice: Subject to any disclaimer, the term of this patent is extended or adjusted under 35 U.S.C. 154(b) by 70 days.

(21) Appl. No.: 13/804,142

(22) Filed: Mar. 14, 2013

(65) Prior Publication Data

US 2013/0193378 A1    Aug. 1, 2013

Related U.S. Application Data

(63) Continuation-in-part of application No. 13/278,539, filed on Oct. 21, 2011, now abandoned, which is a continuation-in-part of application No. 12/900,882, filed on Oct. 8, 2010, now Pat. No. 8,414,689.

(60) Provisional application No. 61/252,838, filed on Oct. 19, 2009, provisional application No. 61/695,556, filed on Aug. 31, 2012.

(51) Int. Cl.
   *B01J 41/04*     (2006.01)
   *B01D 53/02*    (2006.01)
   *C07C 7/12*     (2006.01)
   (Continued)

(52) U.S. Cl.
   CPC ............... *B01J 41/046* (2013.01); *C07C 7/12* (2013.01); *C10G 25/02* (2013.01); *Y02C 10/08* (2013.01); *B01J 49/0013* (2013.01); *B01J 49/0095* (2013.01); *B01D 53/02* (2013.01); *B01D 53/0462* (2013.01); *B01D 53/047* (2013.01); *B01D 2253/206* (2013.01); *B01D 2257/504* (2013.01); *B01D 2258/0283* (2013.01);
   (Continued)

(58) Field of Classification Search
   USPC ......... 95/96, 98, 99, 105, 106, 114, 115, 135, 95/148; 210/660, 661, 670; 423/242.1, 423/242.7, 244.01; 208/208 R, 250; 585/820, 824, 830
   See application file for complete search history.

(56) References Cited

U.S. PATENT DOCUMENTS 2,713,077 A * 7/1955 Rieve ............................. 208/237
3,282,831 A * 11/1966 Hamm ........................... 210/673
(Continued)

FOREIGN PATENT DOCUMENTS

GB    1296889       11/1972
GB    2157308 A  * 10/1985

OTHER PUBLICATIONS

Zhang X et al; "Studies on the Kinetics of carbon dioxide absorption with immobilised amines (IA)", Chemical Engineering Journal, Elsevier Sequoia, Lausanne, CH, vol. 107, No. 1-3, Mar. 15, 2005, pp. 97-102.

(Continued)

*Primary Examiner* — Frank Lawrence

(57) ABSTRACT

A process for the reduction of carbon dioxide and carbonyl sulfide from various types of gas emitting sources containing carbon dioxide and/or gas or liquid emitting sources containing carbonyl sulfide, using ion exchange resin.

16 Claims, 4 Drawing Sheets

(51) Int. Cl.
*C10G 25/02* (2006.01)
*B01J 49/00* (2006.01)
*B01J 41/12* (2006.01)
B01D 53/04 (2006.01)
B01D 53/047 (2006.01)

(52) U.S. Cl.
CPC ....... *B01D2258/05* (2013.01); *B01D 2257/308* (2013.01); *B01J 41/125* (2013.01); *B01J 49/0056* (2013.01)

(56) References Cited

U.S. PATENT DOCUMENTS

| | | | | |
|---|---|---|---|---|
| 3,284,531 A | * | 11/1966 | Shaw et al. | 585/824 |
| 3,358,421 A | * | 12/1967 | Huxley et al. | 95/11 |
| 3,466,138 A | | 9/1969 | Spiegler et al. | |
| 4,419,245 A | | 12/1983 | Barrett et al. | |
| 4,427,794 A | | 1/1984 | Lange et al. | |
| 4,444,961 A | | 4/1984 | Timm | |
| 5,231,115 A | | 7/1993 | Harris | |
| 5,797,979 A | * | 8/1998 | Quinn | 95/97 |
| 6,245,128 B1 | * | 6/2001 | George, Jr. | 95/186 |
| 6,279,576 B1 | | 8/2001 | Lambert | |
| 2006/0173083 A1 | | 8/2006 | Klipper et al. | |
| 2011/0088550 A1 | * | 4/2011 | Tirio | 95/96 |

OTHER PUBLICATIONS

International Search Report from co-pending Application PCT/US2010051963, dated Jan. 17, 2011, 2 pages.

* cited by examiner

PROCESS AND APPARATUS FOR CARBON DIOXIDE AND CARBONYL SULFIDE CAPTURE VIA ION EXCHANGE RESINS

This application is a continuation-in-part of U.S. application Ser. No. 13/278,539, filed Oct. 21, 2011, now abandoned, which is a continuation-in-part of U.S. application Ser. No, 12/900,882, filed Oct. 8, 2010, now issued as U.S. Pat. No. 8,414,689 on Apr. 9, 2013, and claims the benefit of U.S. Provisional Application No, 61/252,838, filed Oct. 19, 2009, now expired, entitled PROCESS AND APPARATUS FOR CARBON DIOX IDE CAPTURE VIA ION EXCHANGE RESINS, and claims the benefit of U.S. Provisional Application No. 61/695,556, filed Aug. 31, 2012, pending, entitled PROCESS FOR REMOVAL OF CARBONYL SULFIDE FROM HYDROCARBON STREAMS, all of which are incorporated herein by reference in their entirety.

The present invention relates to the removal of carbon dioxide (or $CO_2$) from various types of gas emitting sources containing carbon dioxide, especially to the removal of carbon dioxide from industrial gas emitting sources, via the use of an ion exchange material, as well as the removal of carbonyl sulfide ("COS") using the ion exchange material from gas sources containing carbonyl sulfide and from liquid sources containing carbonyl sulfide.

Applicant has now found the use of an ion exchange material comprising an aminoalkylated bead polymer in the removal of carbon dioxide and/or carbonyl sulfide from industrial applications, as compared to other materials often used in removal applications.

There is broadly contemplated, in accordance with at least one embodiment of the present invention, a process for removing carbon dioxide from a carbon dioxide containing gas stream, comprising: providing an ion exchange resin, contacting said ion exchange resin with said carbon dioxide containing gas stream, sorbing a portion of said carbon dioxide from the carbon dioxide containing gas stream by the ion exchange resin, thereby forming a carbon-dioxide-form ion exchange resin, and de-sorbing the attached carbon-dioxide from the carbon-dioxide-form ion exchange resin, thereby increasing the capacity of the ion exchange resin to re-sorb carbon dioxide.

There is also broadly contemplated, in accordance with at least one embodiment of the present invention, a process for removing carbonyl sulfide from a carbonyl sulfide containing gaseous or liquid stream, comprising: providing an ion exchange resin, contacting said ion exchange resin with said carbonyl sulfide containing gaseous or liquid stream, sorbing a portion of said carbonyl sulfide from carbonyl sulfide containing gaseous or liquid stream by the ion exchange resin, thereby forming a carbonyl-sulfide-form ion exchange resin, and de-sorbing the attached carbonyl sulfide from the carbonyl-sulfide-form ion exchange resin, thereby increasing the capacity of the ion exchange resin to re-sorb carbonyl sulfide.

In another embodiment, the ion exchange resin employed is a weakly basic ion exchange resin. In another embodiment, said ion exchange resin is a polystyrene polymer based resin, which is crosslinked via the use of divinylbenze, and is functionalized with primary amine groups including benzylamine and wherein the resin is produced by a phthalimide process.

In another embodiment of the invention, the aforementioned gas stream is an industrial gas and/or industrial gas stream, such as flue gas streams, hydrocarbon combustion gas streams, natural gas, produced gas, cracked gas, synthesis gas streams, light hydrocarbons such as propane, propylene, ethane, and ethylene, as well as bio-gas streams.

In another embodiment of the invention, the aforementioned liquid stream is an industrial liquid stream, such as, for example, liquefied petroleum gas streams, such as liquefied hydrocarbon streams, for example those from natural gas production, petroleum refining, and/or ethylene production. Examples thereof include streams of propane, propylene, ethane, and/or ethylene primarily in their liquid phase.

In yet another embodiment for the removal of carbon dioxide, the carbon dioxide of said industrial gas and/or gas stream has a partial pressure above 0.05 kPA.

For a better understanding of the present invention, together with other and further features and advantages thereof, reference is made to the following description.

Figure 1:
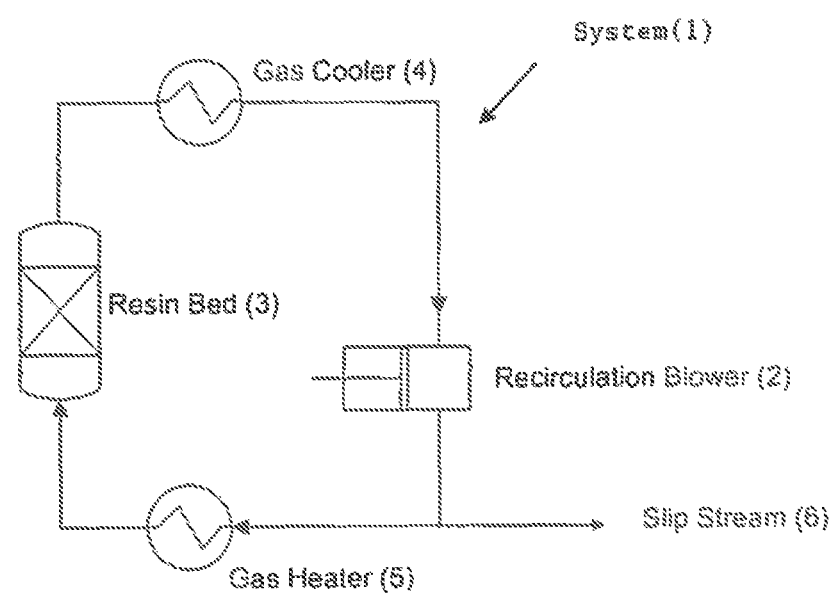
FIG. 1 schematically illustrates a regeneration system for an ion exchanger using a heated carbon dioxide stream.

Although preferred embodiments of the present invention are described herein, it is to be understood that the invention is not limited to those precise embodiments, and that various other changes and modifications may be affected therein by one skilled in the art without departing from the scope or spirit of the invention. Furthermore, while the present invention is described with reference to specific details of particular embodiments and examples thereof, it is not intended that such details be regarded as limitations upon the scope of the invention except insofar as and to the extent that they are included in the accompanying claims.

As used in this specification and the appended claims, the singular forms "a", "an", and "the" include plural referents unless the content clearly dictates otherwise. If not otherwise stated herein, it is to be assumed that all patents, patent applications, patent publications and other publications mentioned and cited herein are hereby fully incorporated by reference herein as if set forth in their entirety herein.

As used herein, sorption shall mean adsorption and/or absorption. And as used herein carbon-dioxide-form ion exchange resin shall mean an ion exchange resin in which a portion of the sites available for sorption comprise carbon dioxide exchangeably bound thereto; and as used herein carbonyl-sulfide-form ion exchange resin shall mean an ion exchange resin in which a portion of the sites available for sorption comprise carbonyl sulfide exchangeably bound thereto.

The bead polymers according to the present invention may comprise those formed of polystyrene polymer resins comprising primary amines and crosslinked via divinylaromatics such as, for example, aminomethylated polystyrene-co-divinylbenzene (i.e., polybenzyl amine-co-divinylbenzene). Furthermore, the ion exchange resins according to the present invention may be monodisperse or heterodisperse and macroporous or gel-types (microporous). Substances are described as monodisperse in the present application in which the uniformity coefficient of the distribution curve is less than or equal to 1.2. The uniformity coefficient is the quotient of the sizes d60 and d10. d60 describes the diameter at which 60% by mass of those in the distribution curve are smaller and 40% by mass are greater or equal. d10 designates the diameter at which 10% by mass in the distribution curve are smaller and 90% by mass are greater or equal.

Monodisperse bead polymers, the precursor of the corresponding monodisperse ion exchange resin, can be produced, for example, by bringing to reaction monodisperse, if desired, encapsulated, monomer droplets consisting of a monovinylaromatic compound, a polyvinylaromatic compound, and an initiator or initiator mixture, and if appropriate a porogen in aqueous suspension. To obtain macroporous bead polymers for producing macroporous ion exchangers, the presence of porogen is utilized.

The various production processes of monodisperse bead polymers both by the jetting principle and by the seed-feed principle are known to those skilled in the art. Reference is made to U.S. Pat. No. 4,444,961, EP-A 0 046 535, U.S. Pat. No. 4,419,245 and WO 93/12167, herein incorporated by reference.

Monovinylaromatic unsaturated compounds used according to the invention comprise compounds such as styrene, vinyltoluene, ethylstyrene, alpha-methylstyrene, chlorostyrene or chloromethylstyrene. Polyvinylaromatic compounds (crosslinkers) used include divinyl-bearing aliphatic or aromatic compounds. For example, use is made of divinylbenzene, divinyltoluene, trivinylbenzene, ethylene glycol dimethacrylate, trimethylol propane trimethacrylate, hexa-1,5-diene, octa-1,7-diene, 2,5-dimethyl-1,5-hexadiene and also divinyl ether.

In addition to the use of aromatic monomers as the starting material for the polymeric ion exchange resin (for example, vinyl and vinylidene derivatives of benzene and of naphthalene (vinylnaphthalene, vinyltoluene, ethylstyrene, alpha-methyl-styrene, chlorostyrenes, and styrene), various non-aromatic vinyl and vinylidene compounds may also be employed. For example, acrylic acid, methacrylic acid, $C_1$-$C_8$ alkyl acrylates, $C_1$-$C_8$ alkyl methacrylates, acrylonitrile, methacrylonitrile, acrylamide, methacrylamide, vinyl chloride, vinylidene chloride, and vinyl acetate.

The subsequent functionalization of the bead polymer ion exchange resin thereby provides a functionalized ion exchange resin that is also generally known to those skilled in the art. For example, US 2006/0173083, hereby incorporated by reference, describes a process for producing monodisperse, macroporous ion exchanges having weakly basic primary amine groups by what is termed the phthalimide process, comprising: a) reacting monomer droplets of at least one monovinylaromatic compound and at least one polyvinylaromatic compound and also a porogen and an initiator or an initiator combination to give a monodisperse crosslinked bead polymer, b) amidomethylating this monodisperse crosslinked bead polymer with phthalimide derivatives, and c) reacting the amidomethylated bead polymer to give a basic ion exchanger having aminomethyl groups in the form of primary amine groups.

A primary amine ion exchanger according to the invention may be produced by the above phthalimide addition process or by the chloromethylation process. As is generally known, the chloromethylation process is one in which a chloromethylate is formed that is subsequently reacted with amines to form an aminomethylated polymer. In one embodiment of the invention, the phthalimide addition process is utilized to produce the ion exchange resin. As a result of the phthalimide addition process for the production of the ion exchange resin, secondary crosslinking is limited as compared to the chloromethylation process. Such secondary crosslinking may occur during the chloromethylation process in which the primary amines of the aminomethylated polymer react to form secondary amines (secondary crosslinking). In one embodiment of the invention, such secondary crosslinking is less than 30% of the formed polymer, and in another embodiment such secondary crosslinking is less than 10%. In yet another embodiment, the secondary crosslinking is less than 5%.

The particle size of the bead polymer formed in the production processes, including those provided above, for example, may be set during polymerization, as well as the bead polymers sphericity. In one embodiment, bead polymers having a mean particle size of approximately 10 to 1000 μm are utilized. In another embodiment of the present invention, a mean particle size of approximately from 100 to 1000 μm is employed. In yet another embodiment, a mean particle size of approximately 100 to 700 μm is used. Further, the bead polymer of the invention may take the form of spherical polymer beads or non-spherical beads (or blocks). In one embodiment, spherical polymer beads are formed.

In one embodiment, the ion exchange resin utilized is a crosslinked, weakly basic, monodisperse, macroporous, spherical, anion exchange polystyrene based resin being functionalized with primary amine groups produced by the phthalimide addition process, for example that which is commercially available from LANXESS Deutschland GmbH under the brand name LEWATIT® VP OC1065.

In one embodiment of the present invention, the aforementioned ion exchange resin is contacted with a gas or gaseous stream comprising carbon dioxide resulting in the sorption of a portion of the carbon dioxide from the gas or gaseous stream and, thereby, reducing the amount of carbon dioxide in the gas or gaseous stream. Industrial sources are of particular applicability for the present invention.

In another embodiment of the present invention, the aforementioned ion exchange resin is contacted with a gas, gaseous stream, or a liquid stream comprising carbonyl sulfide resulting in the sorption of a portion of the carbonyl sulfide from the gas, gaseous stream, or liquid stream and, thereby, reducing the amount of carbonyl sulfide in the gas, gaseous stream, or liquid stream. Industrial sources are of particular applicability for the present invention.

Various areas for application of the present method of carbon dioxide and/or carbonyl sulfide removal from gas streams are made up of a myriad of processes, which may include such gas and gas streams from industrial sources. Industrial gas and/or industrial gas streams may comprise, inter alia, those of or from flue gas streams, hydrocarbon combustion gas streams, natural gas, produced gas, cracked gas, and synthesis gas streams, as well as propane, propylene, ethane, and ethylene streams.

For simplicity, the areas may be broadly divided into energy production and chemical processes. Regarding energy production there is contemplated herein the removal of carbon dioxide found in flue gas produced from electricity generation (for example, steam boilers and combined cycle gas turbines) and steam production for industrial purposes (for example, steam heat and steam turbine drives). Large volumes of hydrocarbon fuel sources, such as coal, petroleum liquids and natural gas, are burned to produce heat and power. The combustion of hydrocarbons with air results in the release of carbon dioxide as a constituent of flue gas into the atmosphere. Illustratively, flue gas from combustion of coal may contain around 15% (by volume) carbon dioxide along with water vapor, nitrogen and other components. While still significant, slightly lower carbon dioxide levels will generally be contained in flue gas from combustion of petroleum liquids and natural gas as a result of their chemical make up.

Another broad energy production area of applicability of the subject invention is the removal of carbon dioxide from natural gas and produced gas. As appreciated by those skilled in the art, natural gas as it is removed from the well may contain varying amounts of carbon dioxide depending upon the well and the methods of enhancing natural gas production. It may often be desirable to reduce the amount of carbon dioxide from the raw natural gas, for example, as away of meeting heat content specifications. In an embodiment of the present invention, there is disclosed a method of carbon dioxide reduction of natural gas via contacting the same with the ion exchange resin of the invention. This process also avoids introducing water vapor to the treated natural gas. As is understood by the skilled artisan, natural gas that is co-produced with petroleum may have much higher concentrations of carbon dioxide either naturally or as a result of enhanced oil recovery techniques that introduce steam and carbon dioxide into the oil well. In many chemical and refinery operations, carbon dioxide is a contaminant that must be removed from various gases, processes and gas streams. Without limitation, several embodiments are readily recognized. For example, in chemical facilities dedicated to producing light olefins, such as ethylene and propylene, carbon dioxide is found in the process gas (normally designated as cracked gas) from the process furnaces where predominantly paraffinic hydrocarbons are thermally cracked with steam to produce unsaturated hydrocarbons. The production of high quality products from these olefins manufacturing plants involves high pressures and low temperatures. In such operations, carbon dioxide in the process gas may cause process inefficiencies and poor product quality if not removed. Broadly, current practices make use of various alkanol amines in the removal of carbon dioxide and other acid gases from the process gas. The instant invention may be used in replace of or in combination with such prior uses. Similarly, in refineries where petroleum is "cracked," thermally and catalytically, carbon dioxide can be present and accumulated in the off gas streams. Upgrading these gases to produce quality products involves carbon dioxide removal where, again, the utilization of the invention may be made.

A further example of chemical operations amenable to at least one embodiment of the instant invention is the purification of propylene used as feedstock for production of polypropylene and other industrial chemicals. The most common routes to propylene are the recovery of the C3 by-products of ethylene production (e.g., propane and/or propylene) through steam cracking and the recovery of the light hydrocarbon cuts from refinery operations of distillation and fluid catalytic cracking. For commercial use, propylene is normally produced to meet one of the following three grades; polymer grade, chemical grade and refinery grade. While the specifications for the three grades of propylene vary from region to region, the grades can be expected to be similar to the following typical specifications of major contaminants. There may be specifications for other components depending on the region and commercial contracts between buyer and seller.

TABLE 1

|  | Polymer Grade | Chemical Grade |
|---|---|---|
| Propylene Content (% weight) | 99.5 minimum | 92 minimum |
| Ethane and Lighter (ppm weight) | 500 | 4000 |
| C4's and Heavier (ppm weight) | 7 | 2000 |
| Acetylenes and Propadiene (ppm Weight) | 5 | 100 |
| Total Sulfur Compounds (ppm weight) | 2 | 10 |
| Propane | Balance | Balance |

Refinery grade propylene can be considered the balance of industrially available propylene streams that do not meet either of the polymer grade or chemical grade specifications. Propylene is a major petrochemical precursor with polypropylene being the largest consumer. Other large scale chemicals produced from propylene include propylene oxide, acrylonitrile, acrylic acid and butanol. In smaller volumes, propylene is used to produce oxo alcohols, cumene for phenol and acetone production and ethylene propylene rubbers.

Another example of a chemical operation to which Applicant's inventive carbon dioxide and/or carbonyl sulfide removal processes may be employed is the production of synthesis gas during the manufacture of ammonia and other valuable products such as, for example, alcohols, aldehydes and other oxygenates. Synthesis gas is generally produced by the partial oxidation of hydrocarbons into hydrogen and carbon monoxide. Such partial oxidation may utilize air, steam or pure oxygen as sources of reactant oxygen and the process may be catalyzed or not. In some operations, additional steam is added to produce additional hydrogen by converting carbon monoxide to carbon dioxide and, concurrently, steam to hydrogen. In all cases, the raw synthesis gas will contain carbon dioxide that must be removed or reduced. Heretofore, the general removal of carbon dioxide was by means of alkanol amines. The amount of carbonyl sulfide present is dependent upon the amount of sulfur containing contaminants found in the feedstocks used for synthesis gas production. Instantly, the present invention may be utilized in which the ion exchange resins are used to remove and/or reduce the carbon dioxide and/or carbonyl sulfide.

Biogas can be broadly defined as the gaseous by-product of the breakdown (thermally, chemically or biologically) of biologically sourced materials. When properly processed, the raw gaseous by-product can be efficiently utilized as fuel similar to natural gas. Raw biogas from anaerobic digestion of organic matter such as mature, agricultural wastes, food wastes, sewage sludge and other biodegradable materials, will be made up of predominantly methane and carbon dioxide and have relatively low fuel value. Fuel value for gas streams is commonly defined as net heating release per unit volume of gas at defined standard conditions of temperature and pressure. Increasing the fuel value of raw biogas can be achieved by reducing its carbon dioxide content.

Another example of a chemical operations to which Applicant's inventive carbonyl sulfide removal processes may be employed are those resulting from various chemical processing activities such as propylene, ethylene, butene or synthesis gas production or consumption, as well as that resulting from hydrocarbon fuel production or consumption, for example liquefied petroleum gas from natural gas production and/or petroleum refining.

As may be appreciated, other processes may exist, especially in industrial settings, which require the removal of carbon dioxide from a gas, gaseous stream, or other environment, as well as the removal of carbonyl sulfide from gas, gaseous stream, or liquid streams. As such, the use of the presently disclosed ion exchange resin in accord with the above stated principles related thereto may be employed.

While it can be appreciated that the concentration of carbon dioxide in such industrial processes may vary greatly, in the aforementioned industrial gases and gas streams, carbon dioxide generally comprises an appreciable part of the total gas and/or gas stream. Illustratively, produced natural gas from oil wells employing enhanced oil recovery techniques may contain around 40% (v/v) carbon dioxide, similar to carbon dioxide content of raw biogas. Flue gas streams, for example from boilers, may contain carbon dioxide being around 15% (v/v) of the gas stream. In some other chemical processes, carbon dioxide may be undesirable in as little amount as from 1 to 2% (v/v), thus requiring its removal and/or reduction.

In one embodiment of the present invention, the use of the ion exchange for the reduction of carbon dioxide is employed in an industrial gas and/or gas stream in which the carbon dioxide has a partial pressure above 0.05 kilopascals (kPA). Industrial application of the subject invention is to broadly include systems in which the carbon dioxide concentration is about ten times the concentration of carbon dioxide in a non-industrial application, such as, for example, in the purification of air in a closed environment for human breathing.

In yet another embodiment, the removal of carbonyl sulfide in industrial gases and/or liquids and/or fuel gases and/or liquids having a measurable concentration of carbonyl sulfide through use of the polybenzylamine ion exchange resin.

A non-limiting example of the suspected reaction of an aminoalkylated polymer and carbon dioxide can be represented as follows wherein a poly-benzylamine material is reacted with carbon dioxide yielding a poly-benzylcarbamic acid compound:

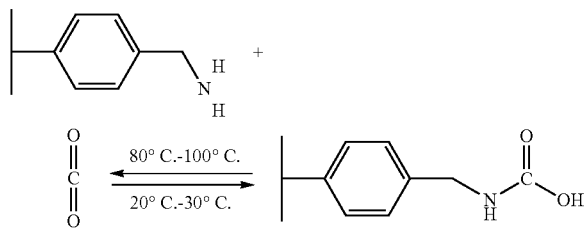

A non-limiting example of the suspected reaction of an aminoalkylated polymer and carbonyl sulfide can be represented as follows wherein a poly-benzylamine material is reacted with carbonyl sulfide yielding a poly-thiocarbamic acid compound:

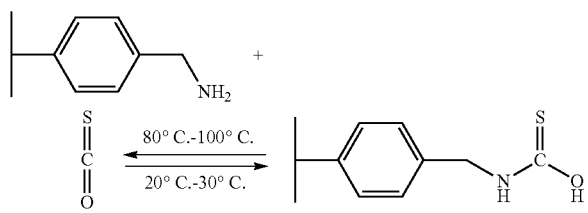

The primary amine ion exchange resin of the present invention can be used in fixed or fluidized beds and can be regenerated to a carbon dioxide lean and/or carbonyl sulfide lean condition, as the case may be, through use of heat (designated as thermal swing adsorption (TSA)), vacuum (designated as pressure swing adsorption (PSA)) and/or a combination of heat and vacuum.

It has also been found that the use of partially dried primary amine ion exchange resin may have a greater ability to adsorb gaseous carbon dioxide, as well as carbonyl sulfide, and subsequently reduce regeneration energy requirements. While, as best understood, water does not take part in the above disclosed reactions, completely drying the ion exchange material can negatively affect the performance and thus an optimum moisture content may be employed.

Without being limited to any particular theory, completely drying the primary amine ion exchange resin may cause the micropores of the material to collapse, thereby, effectively stopping the resin's ability to adsorb carbon dioxide and/or carbonyl sulfide. Sorption performance, however, returns when the resin beads are rehydrated to between 5% by weight and 10% by weight water content, based on the total weight of the resin. Increasing the water content above 10% by weight does not enhance microporosity and unnecessarily increases regeneration heat requirements.

Both the poly-benzylcarbamic acid compound and the poly-thiocarbamic acid compound of the reactions disclosed above are found to be unstable at slightly elevated temperatures. While a modicum amount of captured carbon dioxide and/or carbonyl sulfide can be recovered from the saturated primary amine ion exchange resin by reducing pressure, more efficient desorption can be effected by the application of heat, thereby raising the saturated resin temperature to approximately 100° C. At which point captured carbon dioxide and carbonyl sulfide, respectively, will return to the gas phase within and around the resin beads and thence flow to an area of lower pressure. Greater pressure difference between the gas surrounding the warm resin beads and the down stream carbon dioxide and/or carbonyl sulfide dispersal area will increase the desorption efficiency and reduce the time required for regeneration. Hence, thermal swing operation supplemented with pressure swing adsorption constitutes the optimal process for carbon dioxide and carbonyl sulfide sorption. As mentioned earlier, regeneration of carbon dioxide and/or carbonyl sulfide rich resin to the carbon dioxide and/or carbonyl sulfide lean resin form can be accomplished via the application of heat to the carbon dioxide and/or carbonyl sulfide rich resin to break the attraction/bonding between the resin and carbon dioxide and/or carbonyl sulfide, respectively. This heat can be delivered through convective, conductive or radiant heat transfer methods. The optimal choice of heat transfer will be determined by many factors that pertain to the physical limitations of the resin, the adsorption and regeneration processes and the quality and quantity of heat available as well as other considerations understood by those knowledgeable of the art.

As used herein carbon dioxide and/or carbonyl sulfide rich and carbon dioxide and/or carbonyl sulfide lean are generally understood to mean the condition where the ion exchange resin contains a relatively increased amount of carbon dioxide and/or carbonyl sulfide, respectively and the condition where the ion exchange resin contains a relatively reduced amount of carbon dioxide and/or carbonyl sulfide, respectively.

In some instances, the purity of carbon dioxide recovered in the regeneration step may be of great importance. For example, the use of captured carbon dioxide in tertiary oil recovery where moisture free high purity carbon dioxide has distinct advantages. To recover high purity carbon dioxide, the heat source may be hot carbon dioxide used to raise the temperature of carbon dioxide rich resin. In such a system carbon dioxide liberated from the resin will join the heat stream of carbon dioxide and flow away from the warm resin. A slip stream of carbon dioxide can be removed from the bulk stream that is then reheated and used to regenerate other carbon dioxide rich resin.

In FIG. 1 there is illustrated one embodiment of a system (1) for the regeneration of an ion exchanger with heated carbon dioxide. A shown, the system has interconnected to one another a recirculation blower (2), a resin bed (3), a cooler (4), a heater (5) and a slip stream opening (6). A carbon dioxide stream is then re-circulated through the system and/or discharged from the system.

As shown, the recirculation blower (2) is employed to sufficiently raise the pressure of the recirculating carbon dioxide stream to allow the stream to pass through the heat exchange equipment and the resin bed (3), which is optionally a fixed bed or fluidized bed. Heated carbon dioxide from the heater (5) flows into the resin bed (3) and warms the bed to release sorbed carbon dioxide from the resin. The mass of carbon dioxide flowing from the resin bed (3) will be greater than the amount of carbon dioxide flowing into the resin bed by the amount of carbon dioxide liberated from the resin. The resin bed effluent carbon dioxide may be cooled via the cooler (4) depending upon the processing equipment requirements. The combined stream from the cooler (4) flows to the blower (2) and a slip stream of liberated carbon dioxide is removed from the regeneration process via the slip stream opening (6) to maintain material balance and pressure integrity.

In another embodiment (not shown) of the above process both the cooler and the heater are eliminated from the system, for example wherein a high temperature blower is utilized.

It should be appreciated, that the particle size, particle size distribution, and sphericity of the ion exchange resins are all factors that may be varied to contribute to optimal performance with respect to adsorption and desorption kinetics, as well as hydraulic characteristics in industrial applications. In the complete process comprising a sorption vessel and a desorption vessel, one may be a fixed bed and the other may be a fluidized bed. In this specific case, the particle size, particle size distribution and sphericity of the ion exchange resin utilized may depend upon process design and economic requirements.

In an embodiment of the present invention there is disclosed the need to dry the adsorbent prior to its use. For example, it may be understood from the above illustrative reaction that the poly-benzylamine material can be regenerated with heat, thus lending itself to thermal swing adsorption. Heat requirements for regeneration of the resin are low due to the physical and chemical nature of the resin. On a weight basis, the resin will have roughly one quarter the heat requirements of water for a given temperature rise. Subsequently, a wet resin will require a greater amount of energy for regeneration because of the thermal requirements of water.

EXAMPLES

Figure 2:
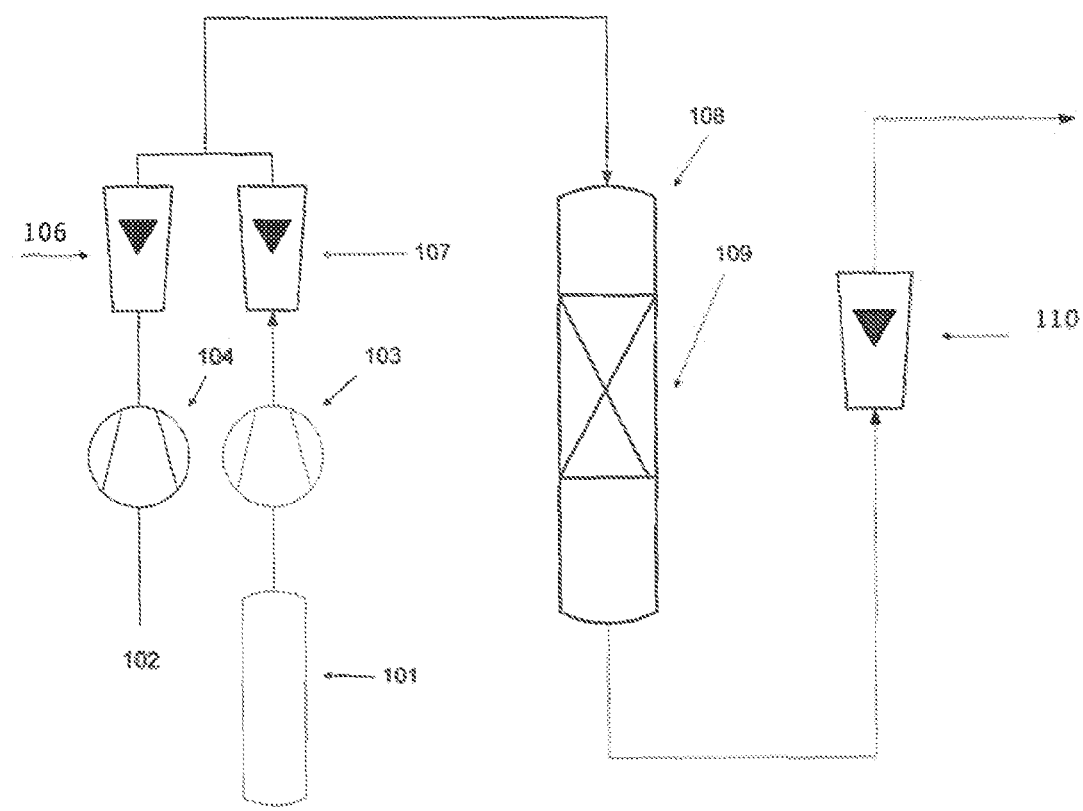
FIG. 2 schematically illustrates the laboratory equipment employed in the examples set forth herein.

Various laboratory experiments were performed utilizing ion exchange resin material for the removal of carbon dioxide and carbonyl sulfide from gaseous streams. The laboratory test equipment is illustrated in FIG. 2. The results of these experiments are summarized in FIGS. 3 and 4.

Referring to FIG. 2, the same apparatus was used for both carbon dioxide and carbonyl sulfide adsorption testing. Applicants note, the experimental description provided herein is with reference to carbon dioxide capture, however, the description is analogously applicable for the testing of carbonyl sulfide capture.

Carbon dioxide gas is stored in pressurized gas cylinder 101 and fed to metering pump 103. Air 102 at atmospheric conditions is fed to metering pump 104. Individual volumetric flows of air and $CO_2$ gas are measured in rotameters 106 and 107, respectively. The flows are combined and directed to reactor vessel 108. This reactor contains a fixed bed of benzyl amine co-polystyrene ion exchange resin 109. The ion exchange resin readily adsorbs carbon dioxide. The gas stream leaving reactor vessel 108 is measured by rotameter 110.

The reactor was charged with 5 grams of dried benzyl amine co-polystyrene resin. The commercially available resin used in the experiment is Lanxess Deutschland GmbH LEWATIT® VP OC1065. The volumetric flow rates of air and carbon dioxide were controlled to be approximately equal at 1.3 liters per hour.

Figure 3:
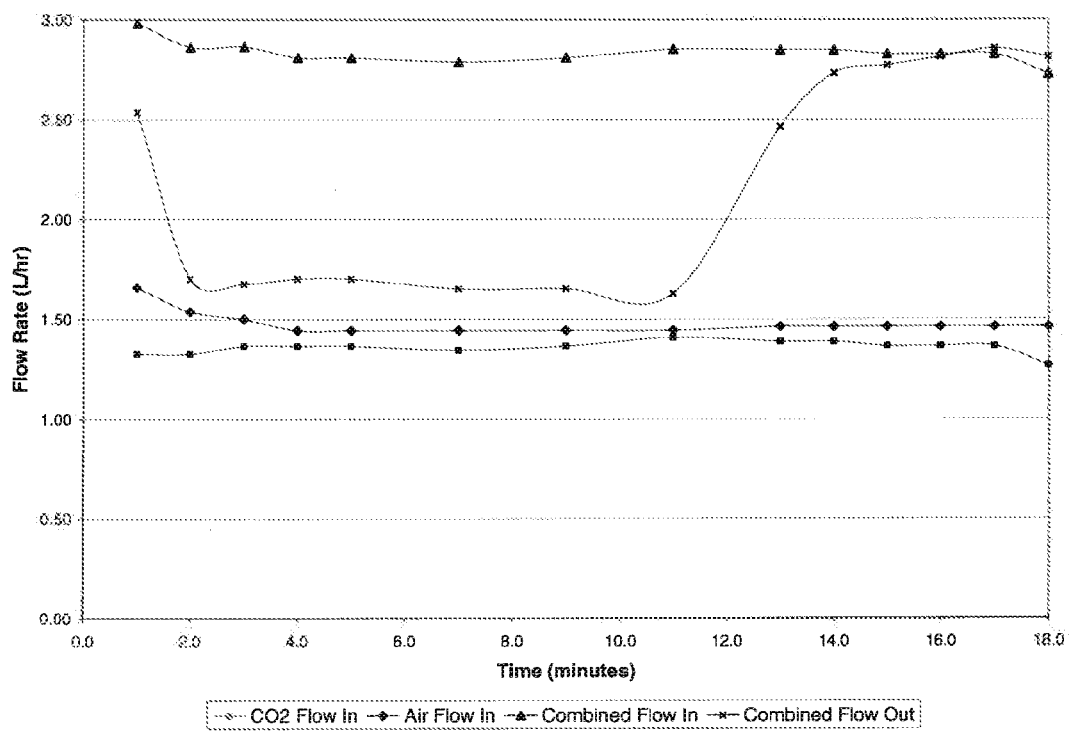
FIG. 3 schematically illustrates the results of passing a gas stream containing carbon dioxide over a benzyl amine-co-polystrene based resin produced by a phthalimide addition process.
Figure 4:
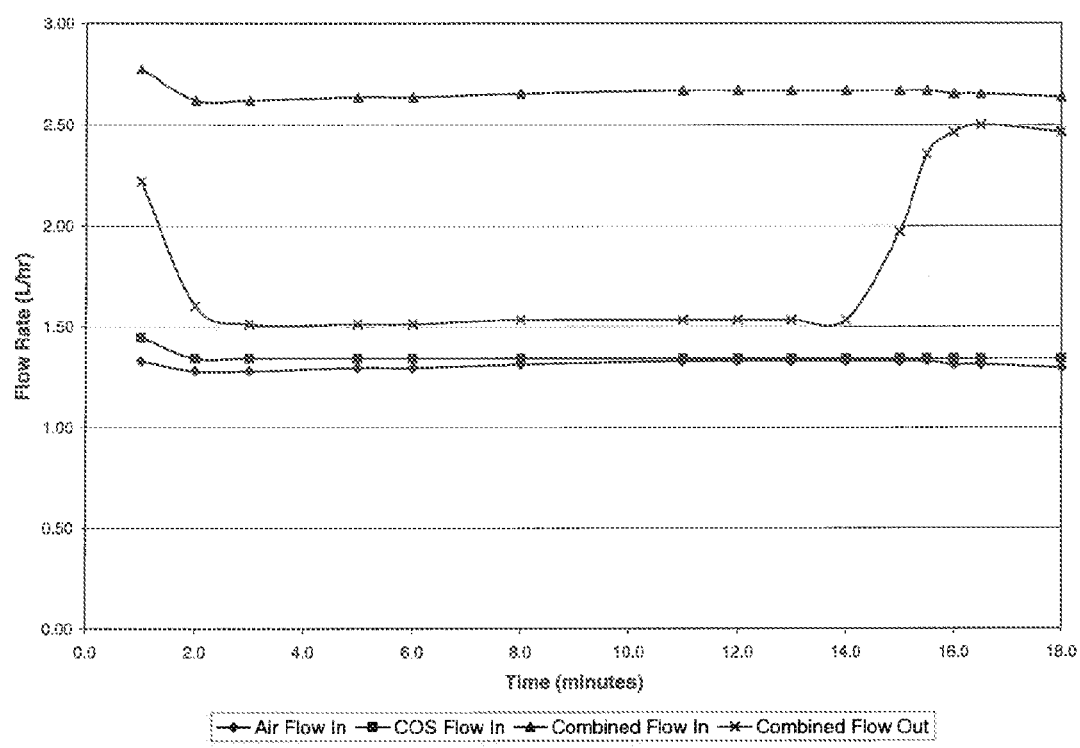
FIG. 4 schematically illustrates the results of passing a gas stream containing carbonyl sulfide over a benzyl amine-co-polystrene based resin produced by a phthalimide addition process.

The results are illustrated graphically in FIGS. 3 and 4. The outlet gas stream flow rate is markedly less than the inlet gas stream flow rate from around 3 minutes of operation until around 14 minutes of operation. The difference can be interpreted as the adsorption of carbon dioxide on the resin. By weighing the $CO_2$ loaded resin, it was calculated that the resin adsorbed 0.009 gram moles of carbon dioxide. When the experiment was separately performed for carbonyl sulfide removal, the resin adsorbed 0.006 gram moles of carbonyl sulfide.

We claim:

1. A process for removing carbonyl sulfide from a carbonyl sulfide containing fluid stream, the process comprising:
   contacting the carbonyl sulfide containing fluid stream and a benzyl amine-co-polystrene based ion exchange resin,
   sorbing at least a portion of the carbonyl sulfide from the carbonyl sulfide containing stream by the on exchange resin, thereby forming a carbonyl-sulfide-form ion exchange resin, and
   desorbing the attached carbonyl sulfide from the carbonyl-sulfide-form ion exchange resin by one of: heat, or heat and vacuum, thereby increasing the capacity of the resin to re-adsorb carbonyl sulfide.

2. The process according to claim 1, wherein the carbonyl sulfide stream is a gaseous stream.

3. The process according to claim 2, wherein the gaseous stream is from a synthesis gas stream or a light hydrocarbon gas stream.

4. The process according to claim 3, wherein the light hydrocarbon gas stream is a propane, propylene, ethane, and/or ethylene gas stream.

5. The process according to claim 1, wherein the carbonyl sulfide stream is a liquid stream.

6. The process according to claim 5, wherein the liquid stream is a liquefied petroleum gas stream.

7. The process according to claim 6, wherein the liquefied petroleum gas stream is a propane, propylene, ethane, and/or ethylene liquefied stream.

8. The process accordingly to claim 1, wherein the benzyl amine-co-polystrene based resin is produced by a phthalimide addition process.

9. The process according to claim 1, wherein the carbonyl sulfide sorbing and desorbing steps are primarily thermal swing driven operation steps.

10. The process according to claim 1, wherein the carbonyl sulfide sorbing and desorbing steps are driven by a thermal swing operation in combination with a pressure swing operation.

11. The process according to claim 1, wherein said ion exchange resin has a water content between about 1% by weight and 25% by weight, based on the total weight of the resin.

12. The process according to claim 1, wherein said ion exchange resin has a water content of greater than about 5% by weight and less than about 15% by weight, based on the total weight of the resin.

13. The process according to claim 1, wherein the on exchange resin comprises beads having a mean particle size of approximately 10 to 1000 μm.

14. The process according to claim 1, wherein the on exchange resin comprises beads having a mean particle size of approximately 100 to 1000 μm.

15. The process according to claim 1, wherein the ion exchange resin comprises beads having a mean particle size of approximately 100 to 700 μm.

16. The process according to claim 1, wherein the ion exchange resin comprises beads having a uniformity coefficient of the distribution less than or equal to 1.2.

* * * * *